United States Patent
Kaltenbeck et al.

(10) Patent No.: US 7,867,375 B2
(45) Date of Patent: Jan. 11, 2011

(54) METHOD FOR DETECTING THE PRESENCE OR ABSENCE OF A GAS BUBBLE BY DYNAMIC SENSOR RESPONSE

(75) Inventors: Heinz Kaltenbeck, Graz (AT); Robert Grübler, Graz (AT); Egon Landschützer, Graz (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1063 days.

(21) Appl. No.: 11/216,765

(22) Filed: Aug. 31, 2005

(65) Prior Publication Data

US 2006/0213773 A1    Sep. 28, 2006

(30) Foreign Application Priority Data

Sep. 2, 2004    (AT) ................ 1468/2004

(51) Int. Cl.
*G01N 27/407* (2006.01)
(52) U.S. Cl. ............... 205/775; 205/782; 204/431
(58) Field of Classification Search ............ 204/410, 204/411, 421–429; 205/781, 783.5–785, 205/787; 436/1–181; 324/691–724; 422/68.1–98; 600/309–367
See application file for complete search history.

(56) References Cited

U.S. PATENT DOCUMENTS

| | | | |
|---|---|---|---|
| 3,874,850 A | | 4/1975 | Sorensen et al. |
| 3,961,898 A | | 6/1976 | Neeley et al. |
| 4,358,423 A | | 11/1982 | Nedetzky |
| 5,061,631 A | * | 10/1991 | Calabrese .......... 436/11 |
| 5,763,760 A | * | 6/1998 | Gumbrecht et al. ......... 73/1.06 |
| 2003/0080002 A1 | * | 5/2003 | Taagaard et al. ........... 205/782 |

FOREIGN PATENT DOCUMENTS

| | | |
|---|---|---|
| AT | 12502003 A | 8/2004 |
| EP | 0355896 A2 | 2/1990 |
| EP | 0 484 876 B1 | 7/1997 |
| EP | 1084963 A2 | 3/2001 |
| EP | 1 394 534 A2 | 3/2004 |
| WO | WO 01/33195 A1 | 5/2001 |

OTHER PUBLICATIONS

Linke, V., Vacek, V., Sinkule, J., Benes, P., "Measurement of Oxygen by Membrane-Covered Probes: Guidelines for Applications in Chemical and Biochemical Engineering", Ellis Horwood Limited, 1988, pp. 91-93.

* cited by examiner

*Primary Examiner*—Nam X Nguyen
*Assistant Examiner*—Gurpreet Kaur
(74) *Attorney, Agent, or Firm*—Thomas E. Lees, LLC

(57) ABSTRACT

A method for detecting the presence or absence of a gas bubble in an aqueous liquid is provided comprising providing a sensor positioned within a measuring chamber, wherein the sensor is configured to determine the concentration of a gaseous component dissolved in a liquid, the sensor comprising a sensitive region; setting a gas partial pressure at the sensor, wherein the gas partial pressure differs from an expected value of the gas partial pressure of the gaseous component of a liquid to be measured; exposing the sensor to the liquid to be measured; resting the liquid until standstill is attained; recording a signal from the sensor as a function of time until the signal becomes constant; and detecting the presence or absence of a gas bubble from the variation of the signal over time. The gas bubble, if present, is in at least partial contact with the sensitive region of the sensor.

19 Claims, 2 Drawing Sheets

METHOD FOR DETECTING THE PRESENCE OR ABSENCE OF A GAS BUBBLE BY DYNAMIC SENSOR RESPONSE

CROSS-REFERENCE TO RELATED APPLICATION

This application claims priority to Austrian patent application no. A 1468/2004 filed 2 Sep. 2004, the disclosure of which is incorporated herein by reference.

BACKGROUND OF THE INVENTION

The present invention relates to analysis systems and methods thereof, and in particular to a method for detecting the presence or absence of a gas bubble in an aqueous liquid.

For the purposes of clinical diagnosis analysing systems are used for blood-gas analysis or for other measurements in liquid samples. Such systems are employed for instance for the determination of the partial pressure of oxygen or of carbon dioxide in blood, or of the hemoglobin parameters of whole blood, and for measurement of pH-value or ion concentration or special metabolites.

Complex analysis systems of this kind are usually provided with different sensor elements for determination of the parameters of interest, which elements are used for a multitude of measurements. Such sensor elements are for instance electrochemical or optical sensors for the determination of gas values, of the pH-value, of ion values or metabolite values, or optical measuring units for the determination of hemoglobin values.

In electrochemical gas sensors, also known as gas-selective or gas-sensitive electrodes, the gas molecules to be determined diffuse from an usually aqueous exterior solution or a gas phase into the interior electrolyte chamber of the sensor via a gas-permeable but essentially fluid- and ion-impermeable membrane. In addition to a liquid or solid interior electrolyte layer, the interior electrolyte chamber contains electrodes for electrochemical determination of the gas, especially measuring or working electrodes, counter-electrodes and reference electrodes. In the interior electrolyte chamber the electrochemical reactions for the determination of the gas by means of amperometric or potentiometric methods take place.

In the case of optical-chemical sensors a number of widely differing design variants and measurement principles have become known. In contrast to electrochemical sensors optical sensors do not require a reference electrode. An optical-chemical sensor typically consists of one or more layers of inorganic and/or organic, typically polymeric, substances applied on a transparent substrate, where at least one layer contains a dye whose optical properties (e.g., absorption, luminescence, etc.) are dependent on an analyte contained in the sample medium.

A frequently used gas sensor is the Clark oxygen sensor, for instance, where a gas-permeable membrane separates the interior electrolyte solution from the aqueous exterior medium, i.e., the medium to be measured. In the simplest case two electrodes dip into the interior electrolyte solution, one of which is placed immediately behind the membrane as a working electrode. After a polarization voltage of suitable strength has been applied, the oxygen which has diffused through the membrane from the measurement medium into the interior electrolyte chamber, is consumed by electrochemical reduction at the working electrode and an electric current corresponding to the substance consumed flows. This current is proportional to the partial pressure of oxygen in the medium to be measured and represents the primary measurement quantity.

Other frequently employed electrochemical gas sensors with gas-permeable membranes are for instance potentiometric sensors of the Severinghaus type for the measurement of carbon dioxide or electrochemical sensors for the determination of hydrogen by means of oxidation on platinum electrodes.

Such electrochemical gas sensors are often used in medical and diagnostic analyzers for the determination of partial gas pressures or gas concentrations in liquids. In particular, they are employed in blood gas analyzers, which play an important role in medical diagnostics. Blood gas analyzers often are provided with a plurality of sensors for diverse parameters, which are arranged in series. The sample fluid flows through these sensors, measurement often being taken by the "stop-flow-method", i.e., with the sample at standstill during the measurement proper. Systems of this type are often used for routine measurements in clinics, laboratories and by medical practitioners, thus requiring the sensors used to have long service life, high accuracy and good reproducibility.

For the determination of oxygen in the OMNI® analyzer systems of Roche Diagnostics GmbH (Graz, Austria), for example, amperometric $O_2$-sensors and potentiometric $CO_2$-sensors are used. The oxygen sensors are miniaturized gas sensors of the Clark type. These gas sensor elements comprise, besides the actual sensor with its interior electrolytic chamber containing the electrodes, a sample passage for the transport and intermediate storage of the sample. Between the interior electrolytic chamber and the sample passage there is a gas-permeable and essentially ion- and fluid-impermeable plastic membrane separating the interior electrolytic chamber from the sample passage. The membrane is provided in a mechanically stretched state.

Frequently thin plastic membranes are employed in electro-chemical gas sensors, with layer thicknesses in the micrometer range, which are made from hydrophobic plastic materials, especially from polytetrafluoroethylene, polypropylene and polyethylene. Further details concerning typical membrane materials may be found in "Measurement of Oxygen by Membrane-covered Probes" (Ellis Horwood series in analytical chemistry, 1988, Ellis Horwood Limited, page 91f).

When gaseous analytes are determined in aqueous solutions by means of electrochemical gas sensors, especially in physiological fluids such as whole blood, serum or urine, problems may occur in certain rare cases during sample measurement or during calibration or quality control, if the sample or the calibrating or control medium does not completely fill the sample passage or if the solution contains gas bubbles, e.g., air bubbles, in the region of the sensors. Especially in blood-gas analyzer systems with sensor elements for small sample volumes gas bubbles may cause measurement errors, which will necessitate efficient checking for the presence or absence of gas bubbles in this case. Gas bubbles mostly adhere to the membrane surface. This phenomenon is observed when during the filling process of the sample passage the aqueous fluid avoids the hydrophobic surface of the membrane on one or both sides. If it is possible for the front of the fluid to laterally bypass the membrane before it is completely covered by the fluid, a gas bubble will form in the area of the membrane. Already existing as well as newly formed gas bubbles will mostly adhere to the membrane and will often not be removed by the fluid flow. A gas bubble adhering to the membrane or remaining in the immediate vicinity of the membrane will result in a measurement error, which will not be recognized as such without additional efforts to detect such bubbles.

The problem of enclosed air bubbles, which cause measurement errors by impeding sufficient wetting of the surface of the sensors used, is pointed out in the prior art. Measures for recognition of such errors will be necessary above all in automated analyzers, where the filling process of the measuring capillary or the absence of bubbles in the sample must be controlled automatically.

Certain known methods cannot efficiently detect air bubbles, however, which do not extend over the whole cross-section of the measuring passage or the measuring capillary. Resistance measurement would in such cases show slight variations in the measurement signal, which however could not be discerned from variations in the signal caused by different conductivity of the individual samples due to differing hematocrit values, for instance.

SUMMARY OF THE INVENTION

It is against the above background that the present invention provides certain unobvious advantages and advancements over the prior art. In particular, the inventors have recognized a need for improvements in methods for detecting the presence or absence of a gas bubble in liquids.

Although the present invention is not limited to specific advantages or functionality, it is noted that the present invention provides a method for the detection of a gas bubble, which typically is in at least partial contact with the sensitive region of a sensor located in a measuring chamber, in such a way that even very small gas bubbles may be definitely detected without additions or changes to the measuring chamber, thus making possible suitable counter measures.

In accordance with one embodiment of the present invention, a method for detecting the presence or absence of a gas bubble in an aqueous liquid is provided comprising providing a sensor positioned within a measuring chamber, wherein the sensor is configured to determine the concentration of a gaseous component dissolved in a liquid, the sensor comprising a sensitive region; setting a gas partial pressure at the sensor, wherein the gas partial pressure differs from an expected value of the gas partial pressure of the gaseous component of a liquid to be measured; exposing the sensor to the liquid to be measured; resting the liquid until standstill is attained; recording a signal from the sensor as a function of time until the signal becomes constant; and detecting the presence or absence of a gas bubble from the variation of the signal over time. The gas bubble, if present, is in at least partial contact with the sensitive region of the sensor.

The method of the invention, in accordance with at least one embodiment, utilizes the fact that gas sensors based on optical-chemical or electrochemical measurement principles have a certain response kinetics of the sensor signal. It is assumed that the gas component to be determined by the sensor is also present in the gas bubble.

Thus amperometric $O_2$-sensors require a certain time for the signal to change from a first signal value corresponding to a preset $pO_2$, to a second signal value corresponding to the $pO_2$ of the sample. The response kinetics is slower if the $O_2$-reservoir of the sensor is larger. The $O_2$-reservoir depends on the size of the sensor and the kind of sensor materials in the immediate vicinity of the $O_2$-sensitive elements.

If amperometric $O_2$-sensors are used, in accordance with one embodiment, the method of the invention also utilizes the fact that these sensors consume the analyte ($O_2$) and that $O_2$-depletion in the sample depends on the supply over time of gas molecules in the immediate vicinity of the $O_2$-sensitive elements of the sensor.

According to another embodiment of the present invention, a signal curve value is measured for at least two points in time during the response time of the sensor, and these values are compared with known values obtained from bubble-free samples. In accordance with still another embodiment of the present invention, it is of advantage if, preceding measurement, a gas partial pressure is set at the sensor, which is greater than the gas partial pressure of the gaseous component in the liquid to be measured.

According to yet another embodiment of the present invention, the gas partial pressure at the sensor, preceding the introduction of the liquid to be measured, is set by using an aqueous liquid which contains the dissolved gaseous component to be determined in suitable concentration, for instance a suitably tonometered calibrating, control or rinsing fluid.

In accordance with yet still another embodiment of the present invention, it is also possible to set the gas partial pressure at the sensor, preceding the introduction of the liquid to be measured, by using a gas or mixture of gases which contains the gaseous component to be determined in suitable concentration.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF THE INVENTION

Figure 1:
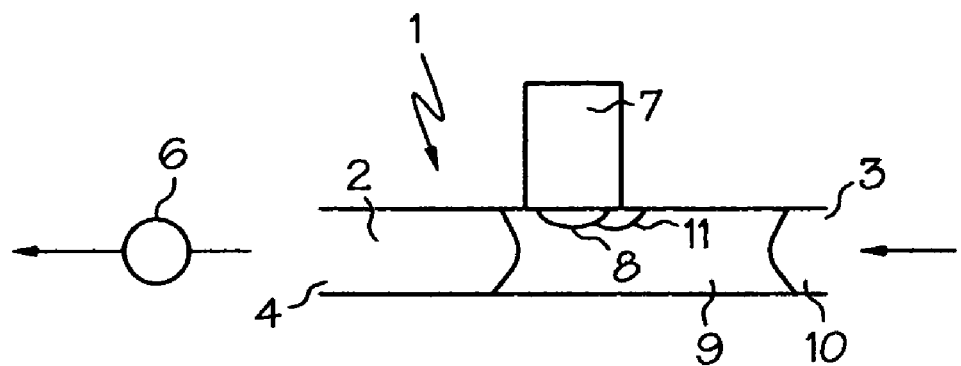
FIG. 1 schematically shows a measuring set-up for the implementation of the method according to one embodiment of the present invention.

The measurement set-up schematically shown in FIG. 1 has a measuring chamber 1 with a through-going sample passage 2 whose inlet opening is indicated by 3. At the outlet opening 4 a pumping or suction device 6 is provided, for instance a peristaltic pump, for transporting the calibrating, control, rinsing or sample fluid. The sample passage 2 may contain a plurality of different electrochemical and/or optical-chemical gas sensors; shown in the figure is an amperometric sensor 7, for instance an $O_2$-sensor, whose sensitive region 8 protrudes into the sample passage 2 and into the measurement liquid 9 (e.g., a calibrating, control, rinsing or sample fluid) contained therein. The measurement liquid 9 can be separated at the inlet side by a separating gas bubble 10 from the subsequent liquid sample. A noxious gas bubble 11 is in at least partial contact with the sensitive region 8 of the amperometric sensor 7.

The method of the invention is particularly suited for measurements in biological fluids, e.g., for in-vitro determination of the $pO_2$ of blood by means of an amperometric $O_2$-sensor (see FIG. 1). In order that the invention may be more readily understood, reference is made to the following example, which is intended to illustrate the invention, but not limit the scope thereof.

Immediately before the sensor 7 is exposed to the measurement fluid 9 (for instance a blood sample) a known $pO_2$ value is set at the sensor. Setting of the $pO_2$ value is performed using a liquid or gaseous medium containing oxygen (e.g., air of the separating air bubble 10 or a suitably tonometered rinsing solution). Typically, an $O_2$ gas partial pressure is set which differs from the expected value of the gas partial pressure of the measurement fluid. In an especially typical way an $O_2$ gas partial pressure is set which is greater than the expected value of the gas partial pressure of the measurement fluid.

Figure 2:
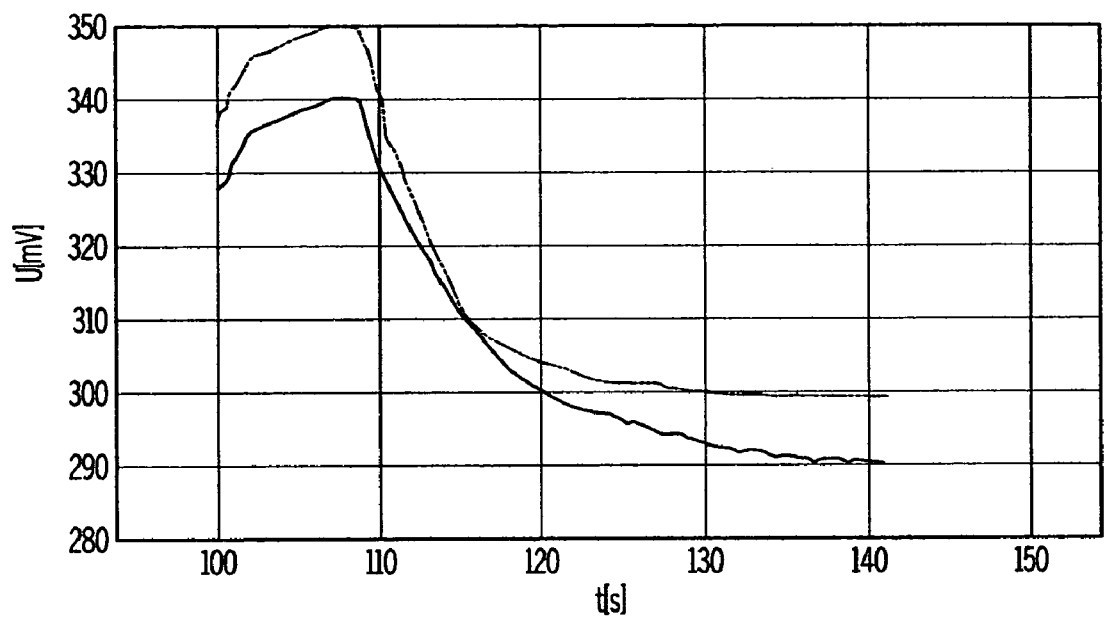
FIG. 2 shows the raw data of the sensor signal over time for a measurement example with and without a gas bubble.

The sensor 7 is exposed to the measurement fluid 9 by filling the sample passage 2 with the measurement fluid 9, rinsing the passage with the measurement fluid if necessary, and then movement of the measurement fluid is stopped at time $t_S$, with the sensor now in contact with the unmoving measurement fluid. The oxygen partial pressure in the sensitive region 8 of the sensor 7 and in the sample will then be equalized through diffusion processes. The signal curve due to the equalizing process is shown in FIG. 2, where the raw data of the signal curve without air bubble (solid line) and with air bubble (dash-dotted line) are shown. Measurement may be continuous, but it is also possible to record only individual pointwise measurement values Sp1 to Sp5 (see FIG. 3) during the response time of the sensor.

Figure 3:
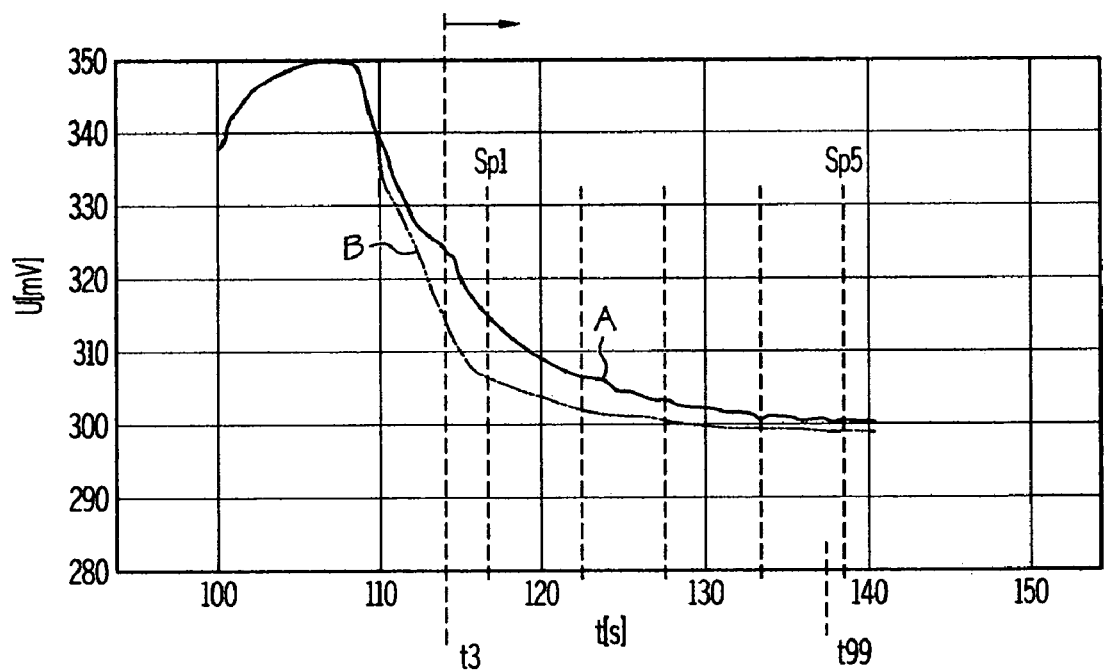
FIG. 3 shows the standardized sensor signals over time of the measurement example from FIG. 2.

FIG. 3 shows the standardized signal curves of the data from FIG. 2, where the measured curves have been standardized in such a way that the curves coincide at time t>150 s. In FIGS. 2 and 3 a voltage U (in mV) proportional to the $O_2$-concentration of the sample, e.g., a blood sample, is plotted on the ordinate versus time t (in s) on the abscissa. The amperometric signal is obtained from a current/voltage converter and measured in the form of a voltage proportional to the current. Evaluation of the signal curves to infer the presence of a gas bubble may be carried out directly from the measured voltage values, converting the signal curves to pressure units ($pO_2$ [mmHg]) and evaluation on the basis of pressure units could be done using calibration data, but is not necessary.

If an amperometric $O_2$-sensor, for instance, is set to a $pO_2$ of ca. 160 Torr with a suitable calibrating medium and is then brought into contact with a blood sample, which has a lower $pO_2$ (e.g., 140 Torr), an exponentially decaying signal curve is observed over the time t. The signal change (dS/dt) tends to zero. Subsequently, $t_{99}$ will designate that period of time during which 99% of the signal change has occurred. The profile of the signal curve mirrors the diffusion processes of oxygen from sensor to sample and vice versa.

The $pO_2$-value of the sensor 7 is to be understood as the $pO_2$ which the materials of the sensor have in the immediate vicinity of the sensitive elements.

When the $pO_2$-value of a blood sample was determined with an amperometric sensor 7, it was unexpectedly found in the measurement situation described above, that in the presence of a gas bubble 11 in direct contact with the sensitive region 8 of the sensor 7 the response behavior of the sensor was faster (see curve B in FIG. 3) than in the absence of the gas bubble (see curve A in FIG. 3). From FIG. 3 it may further be seen that $t_{99}$ is reached sooner if a gas bubble is present. From the difference in the signal curves the presence of a gas bubble may definitely be inferred and suitable counter measures may be taken.

The different signal curves may be explained by differences in diffusion properties, diffusion paths and gas volumes in the presence or absence of a gas bubble. If a gas bubble is present in the immediate vicinity of the sensor, for instance, resulting diffusion paths and gas reservoirs will be different from those in a bubble-free measurement liquid. Inside a gas bubble diffusion kinetics are generally faster than in an aqueous liquid. A gas bubble will generally contain more gas than an equal volume of aqueous liquid.

Figure 4:
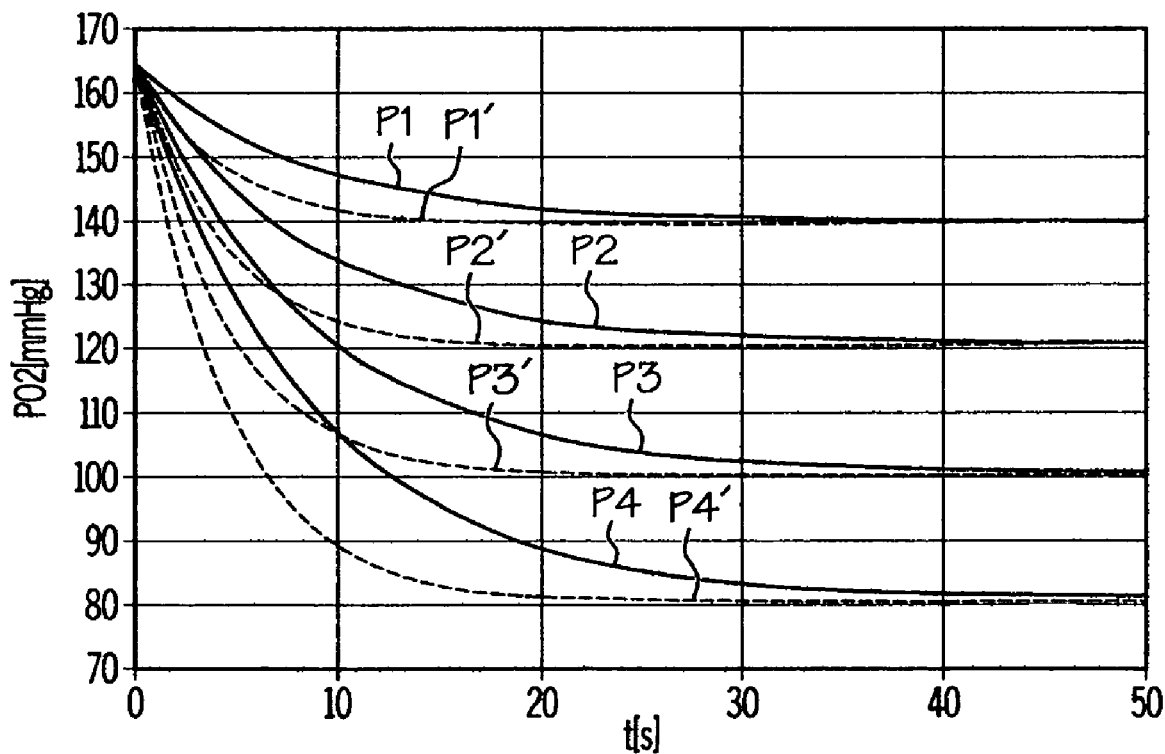
FIG. 4 shows the sensor signal over time for different measurement examples, each with and without a gas bubble.

FIG. 4 shows signal curves for different measurement values, with the voltages being converted to partial pressures ($pO_2$ mmHg) by means of calibration data. From top to bottom the individual curves are as follows:

$P_1$: sample 140 mmHg
$P_1'$: sample 100 mmHg distorted to 140 by air bubble
$P_2$: sample 120 mmHg
$P_2'$: sample 70 mmHg distorted to 120 by air bubble
$P_3$: sample 100 mmHg
$P_3'$: sample 40 mmHg distorted to 100 by air bubble
$P_4$: sample 80 mmHg
$P_4'$: sample 10 mmHg distorted to 80 by air bubble It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A method for detecting the presence or absence of a gas bubble in an aqueous liquid to be measured, comprising:
    providing a sensor positioned within a measuring chamber, wherein said sensor is configured to determine the concentration of a gaseous component dissolved in said liquid to be measured, said sensor comprising a sensitive region;
    setting a gas partial pressure at the sensor to a predetermined value that differs from an expected value of the gas partial pressure of the gaseous component of said liquid to be measured, wherein a time to change from the predetermined value to a gas partial pressure value representative of a bubble-free sample of the liquid to be measured, is known;

exposing said sensor to said liquid to be measured;
resting said liquid to be measured until standstill is attained;
recording a signal from said sensor as a function of time until said signal becomes constant; and
detecting the presence or absence of a gas bubble in said liquid, from a comparison of the variation of said signal over time to said known time to change from said predetermined value to the gas partial pressure value representative of a bubble-free sample.

2. The method of claim 1, wherein said gas bubble is in at least partial contact with said sensitive region of said sensor.

3. The method of claim 1 wherein:
said recording a signal from said sensor as a function of time until said signal becomes constant comprises measuring a signal curve value for at least two points in time during the response time of said sensor, and
said detecting the presence or absence of a gas bubble in said liquid comprises comparing said signal curve values for at least two points in time with said known time to change from the predetermined value to the expected value, where said known time to change is obtained from bubble-free samples.

4. The method of claim 1, wherein said setting a gas partial pressure at the sensor to a predetermined value comprises setting the gas partial pressure preceding measurement, which is greater than the gas partial pressure of the gaseous component in the liquid to be measured.

5. The method of claim 1, wherein an aqueous liquid is used to set the gas partial pressure at the sensor preceding the introduction of the liquid to be measured, wherein said aqueous liquid comprises a suitably tonometered calibrating, control or rinsing fluid.

6. The method of claim 1, wherein said gas bubble is an air bubble.

7. The method of claim 1, wherein said sensor is an amperometric sensor.

8. The method of claim 1, wherein said sensor is a gas sensor.

9. The method of claim 8, wherein said gas sensor is an $O_2$ or $CO_2$ sensor.

10. The method of claim 1, wherein said aqueous liquid to be measured comprises a fluid selected from calibrating fluid, control fluid or sample fluid.

11. The method of claim 10, wherein said sample fluid is a biological fluid.

12. The method of claim 11, wherein said biological fluid is blood.

13. The method of claim 1, wherein the gas partial pressure at the sensor, preceding the introduction of the liquid to be measured, is set by using an aqueous liquid containing the dissolved gaseous component to be determined in suitable concentration.

14. The method of claim 1, wherein the gas partial pressure at the sensor, preceding the introduction of the liquid to be measured, is set by using a gas or mixture of gases containing the gaseous component to be determined in suitable concentration.

15. The method of claim 3, further comprising:
standardizing the measured signal curve with a predetermined curve based upon the known time to change from the predetermined value to the expected value in such a way that the curves coincide at a selected time.

16. The method according to claim 1, wherein:
said recording a signal from said sensor as a function of time until said signal becomes constant comprises:
obtaining said signal from a current/voltage converter measured in the form of voltage proportional to current; and
said detecting the presence or absence of a gas bubble in said liquid to be measured comprises:
converting said signal to pressure units; and
evaluating said signal on the basis of pressure units using calibration data.

17. The method according to claim 3, wherein said response time of said sensor comprises the time until which the signal change tends to zero.

18. The method of claim 1, further comprising:
characterizing the known time to change from the predetermined value to the expected value of the bubble-free sample as a first curve;
wherein:
recording a signal from said sensor as a function of time until said signal becomes constant, comprises characterizing said signal as a second curve that represents a change from said preset partial pressure to the partial pressure of said measurement liquid; and
detecting the presence or absence of a gas bubble in said liquid, comprises comparing at least two values of said first curve to at least two values of said second curve.

19. A method for detecting the presence or absence of a gas bubble in an aqueous liquid to be measured, comprising:
providing a sensor positioned within a measuring chamber, wherein said sensor is configured to determine the concentration of a gaseous component dissolved in said liquid to be measured, said sensor comprising a sensitive region;
setting a gas partial pressure at the sensor to a preset value preceding the introduction of said liquid to be measured, such that said preset value differs from an expected value of the gas partial pressure of the gaseous component of said liquid to be measured, using at least one of:
an aqueous liquid containing the dissolved gaseous component to be determined in suitable concentration; and
a gas or a mixture of gasses containing the gaseous component to be determined in suitable concentration,
wherein a time to change from the preset value to a gas partial pressure value of a bubble-free sample corresponding to the gaseous component of said liquid to be measured is known;
exposing said sensor to said liquid to be measured;
resting said liquid to be measured until standstill is attained;
recording a signal from said sensor as a function of time until said signal becomes constant; and
detecting the presence or absence of a gas bubble in said liquid, from a comparison of the variation of said signal over time to said known time to change from said preset value for the corresponding bubble-free sample.

* * * * *